United States Patent
Hill et al.

(10) Patent No.: US 7,122,040 B2
(45) Date of Patent: Oct. 17, 2006

(54) SUTURE PLACEMENT APPARATUS

(75) Inventors: John Donald Hill, San Francisco, CA (US); Geoff Briggs, Los Altos, CA (US); Michael Sims, Montara, CA (US); Richard C. Fortier, Concord, MA (US); Denis LaBombard, Georgetown, MA (US); Gary R. Whipple, Attleboro, MA (US)

(73) Assignee: J. Donald Hill, San Francisco, CA (US)

( * ) Notice: Subject to any disclaimer, the term of this patent is extended or adjusted under 35 U.S.C. 154(b) by 583 days.

(21) Appl. No.: 10/171,677

(22) Filed: Jun. 17, 2002

(65) Prior Publication Data

US 2002/0193810 A1 Dec. 19, 2002

Related U.S. Application Data

(60) Provisional application No. 60/298,115, filed on Jun. 15, 2001.

(51) Int. Cl.
*A61B 17/04* (2006.01)

(52) U.S. Cl. .................... 606/144; 606/145

(58) Field of Classification Search ............ 289/17; 606/139, 142, 144, 145, 146, 147, 148, 222
See application file for complete search history.

(56) References Cited

U.S. PATENT DOCUMENTS

| | | | |
|---|---|---|---|
| 1,583,271 A * | 5/1926 | Ladislaus | 606/144 |
| 2,008,251 A * | 7/1935 | Hillebrand | 606/146 |
| 3,160,157 A * | 12/1964 | Chisman | 606/223 |
| 3,665,924 A | 5/1972 | Noiles et al. | |
| 3,790,057 A | 2/1974 | Razgulov et al. | |
| 3,908,662 A | 9/1975 | Razgulov et al. | |
| 4,076,162 A | 2/1978 | Kapitanov et al. | |
| 4,349,028 A | 9/1982 | Green | |
| 4,397,311 A | 8/1983 | Kanshin et al. | |
| 4,523,592 A | 6/1985 | Daniel | |
| 4,819,640 A | 4/1989 | Narayanam et al. | |
| 4,873,977 A | 10/1989 | Avant et al. | |
| 4,917,087 A | 4/1990 | Walsh et al. | |
| 4,917,090 A | 4/1990 | Berggren et al. | |
| 4,917,091 A | 4/1990 | Berggren et al. | |
| 5,042,707 A | 8/1991 | Taheri | |
| 5,104,025 A | 4/1992 | Main et al. | |

(Continued)

FOREIGN PATENT DOCUMENTS

EP WO 0067643 11/2000

*Primary Examiner*—Anhtuan T. Nguyen
*Assistant Examiner*—Tuan V. Nguyen
(74) *Attorney, Agent, or Firm*—Baker Botts L.L.P.

(57) ABSTRACT

A suture placement device includes a crook-shaped needle having a suture passage through which a suture thread passes; a suture opening in a tip portion of the needle, from which the suture thread exits the needle; and a bend in the needle including an open portion of the suture passage. The bend defines a suture capture zone in which the suture thread is separated from the needle. A shuttle includes a shuttle body and a shuttle hook. The shuttle hook is formed at a distal end of the shaft. The needle and the shuttle extend from the barrel, and the barrel includes a source of the suture thread and a rotating shaft or cable that causes the shuttle to traverse over the needle. A guide groove guides the shuttle over the needle. The shuttle hook engages the suture thread in the suture capture zone and draws the suture thread to the barrel.

8 Claims, 13 Drawing Sheets

U.S. PATENT DOCUMENTS

| | | |
|---|---|---|
| 5,197,649 A | 3/1993 | Bessler et al. |
| 5,242,457 A | 9/1993 | Akopov et al. |
| 5,346,115 A | 9/1994 | Perouse et al. |
| 5,403,333 A | 4/1995 | Kaster et al. |
| 5,431,322 A | 7/1995 | Green et al. |
| 5,437,681 A | 8/1995 | Meade et al. |
| 5,439,156 A | 8/1995 | Grant et al. |
| 5,456,714 A | 10/1995 | Owen |
| 5,490,856 A | 2/1996 | Person et al. |
| 5,496,334 A | 3/1996 | Klundt et al. |
| 5,540,705 A | 7/1996 | Meade et al. |
| 5,542,949 A | 8/1996 | Yoon |
| 5,643,340 A | 7/1997 | Nunokawa |
| 5,653,717 A | 8/1997 | Ko et al. |
| 5,741,279 A | 4/1998 | Gordon et al. |
| 5,817,113 A | 10/1998 | Gifford, III et al. |
| 5,860,992 A | 1/1999 | Daniel et al. |
| 5,868,763 A | 2/1999 | Spence et al. |
| 5,891,160 A | 4/1999 | Williamson, IV et al. |
| 5,895,395 A | 4/1999 | Yeung |
| 5,904,697 A | 5/1999 | Gifford, III et al. |
| 6,110,187 A | 8/2000 | Donlon |
| 6,165,185 A | 12/2000 | Shennib et al. |
| 6,171,321 B1 | 1/2001 | Gifford, III et al. |
| 6,190,397 B1 | 2/2001 | Spence et al. |
| 6,206,913 B1 | 3/2001 | Yencho et al. |
| 6,241,742 B1 | 6/2001 | Spence et al. |
| 6,251,116 B1 | 6/2001 | Shennib et al. |
| 6,254,618 B1 | 7/2001 | Dakov |
| 6,352,543 B1 | 3/2002 | Cole |
| 6,371,965 B1 | 4/2002 | Gifford, III et al. |
| 2001/0001826 A1 | 5/2001 | Bolduc et al. |
| 2001/0016749 A1 | 8/2001 | Blatter et al. |
| 2001/0023354 A1 | 9/2001 | Blatter et al. |
| 2001/0039424 A1 | 11/2001 | Spence et al. |
| 2001/0039425 A1 | 11/2001 | Dakov |
| 2001/0041902 A1 | 11/2001 | Lepulu et al. |
| 2001/0044631 A1 | 11/2001 | Akin et al. |
| 2001/0047179 A1 | 11/2001 | Gifford, III et al. |
| 2002/0007189 A1 | 1/2002 | Yencho et al. |
| 2002/0022852 A1 | 2/2002 | Dakov |
| 2002/0026137 A1 | 2/2002 | Yencho et al. |
| 2002/0029050 A1 | 3/2002 | Gifford, III et al. |
| 2002/0058955 A1 | 5/2002 | Blatter et al. |

* cited by examiner

FIG. 1

PRIOR ART

SUTURE PLACEMENT APPARATUS

BACKGROUND OF THE INVENTION

1. Field of the Invention

The invention relates to a suture placement apparatus. More specifically, the invention relates to a suture placement apparatus for use in placing sutures in various sites in and around the heart.

2. Description of Related Art

Figure 1:
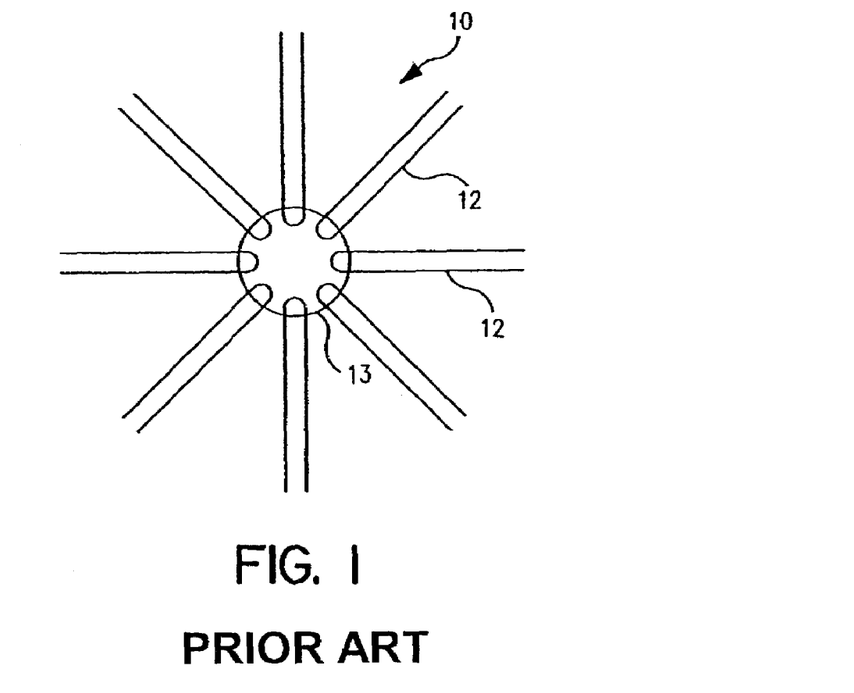
FIG. 1 depicts the placement of sutures around an annulus achieved using known suturing techniques.

In minimally invasive, valve replacement surgery, a plurality of independent suture loops is placed around the annulus of the valve. In the case of the mitral valve, this is the annulus between the left atrium and the left ventricle. Referring to FIG. 1, a sutured annulus 10 is depicted. The placement of suture threads 12 around an annulus 13 is achieved using known suturing techniques. Each suture thread loop is made using a curved needle with suture thread 12 attached. The needle may be gripped with a forceps or other means, introduced intercostally, threaded through annulus 3, and retrieved using the same forceps or another means. Suture thread 12 then is held using a positioner. This process is repeated around annulus 13 until all suture threads 12 are held in the positioner. There may be as many as twenty-four, individual suture thread loops.

An artificial valve has a flange with holes around its perimeter. A surgeon may thread each suture pair through a corresponding pair of holes, slides the valve over the sutures into position at the annulus, and ties the sutures to secure the valve. In order to achieve the desired accuracy and strength of suture placement, considerable time is spent in placing the sutures around the annulus and retrieving them.

SUMMARY OF THE INVENTION

A need has arisen for a suture placement apparatus which will significantly reduce the time required for suture placement and which permits more accurate placement of the suture. It is an advantage of this apparatus that it may be used in suturing replacement valves for the mitral valve and that site is especially significant to the present invention. Nevertheless, there are at least three other sites that are targets for a device incorporating the same concepts of the present device. They are the tricuspid valve, the aortic valve, and the apex of the left ventricle when implanting a left ventricular assist device. It is a further advantage of this apparatus that it reduces the time necessary to prepare a sutured annulus and thereby reduces the duration of the surgery. Moreover, although the structure of the present apparatus has been driven by the requirements of minimally invasive heart surgery, the device also may be used during routine open-heart surgery.

Figure 2:
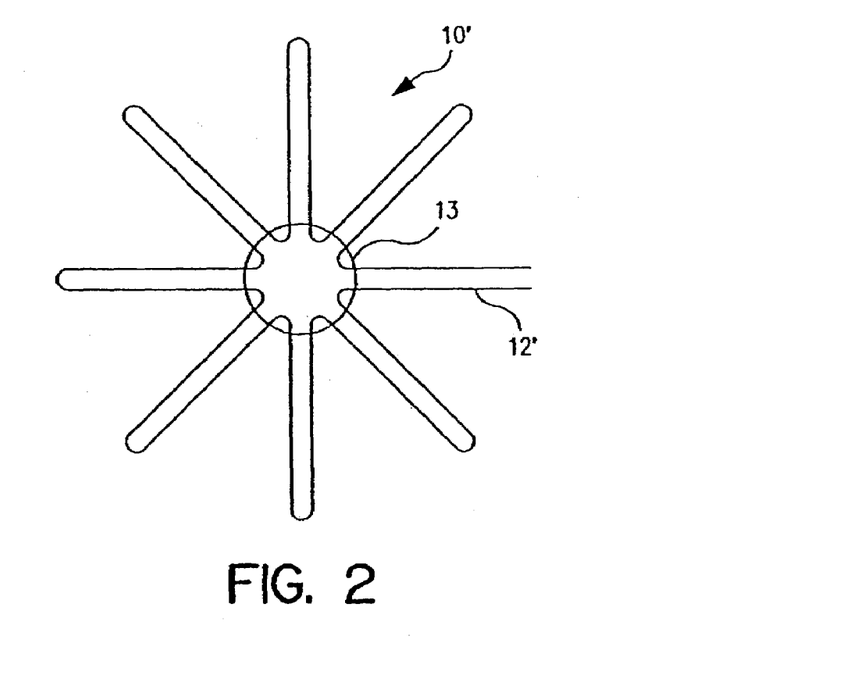
FIG. 2 depicts the placement of sutures around an annulus achieved using the claimed suture placement apparatus.

A further need has arisen for suture placement apparatus, which permits the distal capture of a suture thread loop and its return to a proximal position at which the operator may remove from the apparatus. It is a feature of this apparatus that it comprises a shuttle comprising a hook or hook wire formed on its distal end, which is the suture capturing element. It is an additional feature of the apparatus that it comprises a needle having a bent or curved section, which bent or curved section creates a gap or "capture zone" between the line of the suture thread and the axis of the needle. Referring to FIG. 2, a sutured annulus 10' achieved according to the present invention is depicted. The placement of a suture thread 12' around annulus 13 is achieved using the suture placement apparatus described below. It is an advantage of this apparatus that a single continuous suture thread may be passed through the annulus to secure a replacement valve to the annulus.

Figure 15:
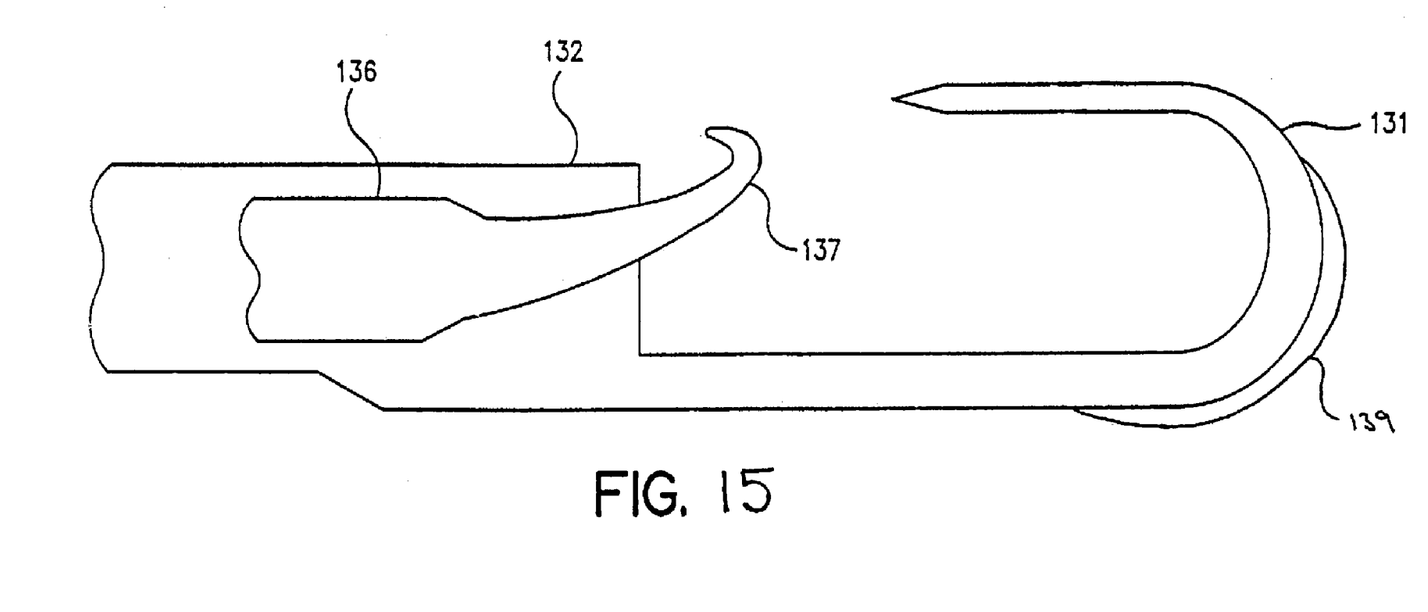
FIG. 15 depicts an needle comprising a rib.

A still further need has arisen for a suture placement apparatus having a stiffened needle. It is a feature of this needle that the distal-most and lower portions have an enlarged rib, such as a rib 139 depicted in FIG. 15, that significantly increases the needle's stiffness. It is an advantage of apparatus with such stiffened needles that the accuracy of the needle placement is significantly increased.

Yet a further need has arisen for a suture placement apparatus having an articulated distal portion of its barrel. It is a feature of this articulated barrel that the distal portion may be rotated upwards or downwards in the plane of the needle. For example, slide button on the handle may control this articulation. It is an advantage of the articulated barrel that it provides the operator with increased visibility when making the needle placements.

In an embodiment of the invention, a suture placement device comprises a crook-shaped needle, a shuttle comprising a shaft and a shuttle hook, a barrel from which the needle extends and the shuttle may be extended, and means for guiding the shuttle. The needle comprises a suture passage through which a suture thread passes; a suture opening in a tip portion (e.g., at or near the tip) of said needle, from which the suture thread exits the needle; and a bend in the needle including an open portion of the suture passage. The bend defines a suture capture zone in which the suture thread is separated from the needle. The shuttle hook is formed at a distal end of the shaft. The barrel comprises a source of the suture thread and means for traversing said shuttle over the needle. The shuttle traverses the needle, and the shuttle hook engages the suture thread in the suture capture zone and draws the suture thread to the barrel.

The means for guiding the shuttle may comprise a ramp formed within the barrel and on which the shuttle rides. As the shuttle distally traverses over the needle, the ramp may guide the shuttle hook through the suture capture zone. As the shuttle proximally traverses over the needle, the shuttle hook may engage the suture thread and draw the suture thread towards and into the barrel.

Alternatively, the means for guiding the shuttle may comprise a ridge formed on the shaft. As the shuttle distally traverses over the needle, the ridge may guide the shuttle hook through the suture capture zone. As the shuttle proximally traverses over the needle, the shuttle hook may engage the suture thread and draw the suture thread towards and into the barrel.

The means for traversing the shuttle over the needle may comprise a lever engaging and driving a plurality of gears in a first direction. The plurality of gears may drive the shuttle to traverse over the needle toward the suture capture zone, and the lever may compress a biasing means, e.g., a spring, that engages and drives the plurality of gears in a second direction opposite to the first direction. The movement of these gears in the second direction may drive the shuttle to traverse over the needle, to engage the suture thread, and to draw the suture thread towards and into the barrel.

Alternatively, the means for traversing the shuttle over the needle may comprise a reversible motor, a screw drive shaft, a threaded passage formed through the shuttle to engage the screw drive shaft, and a guide track. The guide track may prevent the shuttle from rotating as it traverses the needle.

Objects, features, and advantages of the present invention will be understood from the following detailed description of preferred embodiments of the present invention with reference to the accompanying figures.

BRIEF DESCRIPTION OF THE DRAWINGS

Embodiments of the invention are now described with reference to the accompanying figures, which are given by way of example only, and are not intended to limit the present invention.

DETAILED DESCRIPTION OF PREFERRED EMBODIMENTS

Figure 3:
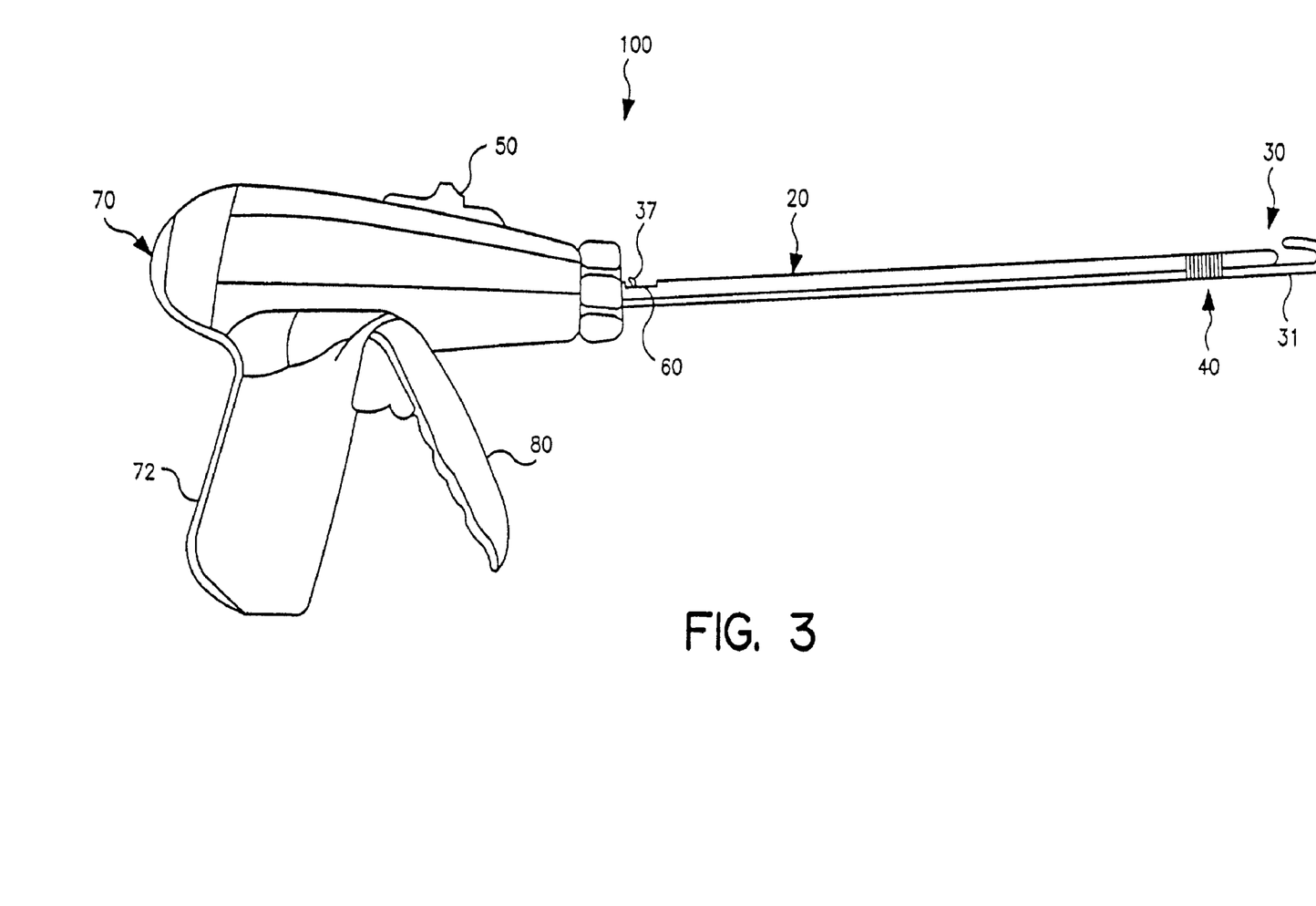
FIG. 3 depicts an embodiment of the suture placement apparatus.

Referring to FIG. 3, an embodiment of a suture placement apparatus 100 according to the present invention is depicted. Apparatus 100 comprises a barrel 20 and a distal portion 30 including a crook-shaped needle 31. A suture thread (not shown), which is coiled around a spool (not shown) at the proximal end of barrel 20, feeds out through needle 31 at or near the tip of needle 31. Distal portion 30 is joined to the remainder of barrel 20 by a flexible coupling 40, which allows an operator to articulate distal portion 30 including needle 31. In this embodiment, a steering slide 50 positioned on a body 70 of apparatus 100 may be moved back and forth, parallel to the axis of barrel 20, in order to control the articulation of distal portion 30 including needle 31.

In addition, a shuttle mechanism (not shown) is adapted to translate through barrel 20 from a proximal end of barrel 20 to distal portion 30. The shuttle mechanism comprises a hook 37 or hook wire, which captures the suture thread after it exits needle 31. Apparatus 100 also includes a grip 72 and a drive lever 80, by which the operator may cause the shuttle to translate distally through barrel 20. After hook 37 has captured the suture thread from needle 31, drive lever 80 may be used to translate the shuttle proximally to a suture pick-up position 60 at the proximal end of barrel 20, so that the suture thread may be removed from hook 37.

As discussed in detail below, drive lever 80 may engage and drive a plurality of gears in a first direction. This plurality of gears may drive the shuttle to traverse needle 31 toward a suture capture zone formed by needle 31. When squeezed, drive lever 80 may compress a spring or other biasing means (not shown). The stored energy in this spring or other biasing means later may be released to drive the plurality of gears in a second direction opposite to the first direction. The movement of these gears in the second direction may drive the shuttle to traverse needle 31, to engage the suture thread, and to draw the suture thread toward the proximal end of barrel 20.

Other means for causing the shuttle and hook 37 to traverse needle 31 are envisioned. For example, apparatus 100 may comprise a compact, battery powered electric motor may be used to drive the shuttle back and forth between the proximal and distal positions. Such a motor may be coupled to a drive shaft or lead screw, extending the length of barrel 20. As described below with respect to FIGS. 12A and 12B, the shuttle may include a threaded passage which is engaged by the drive shaft, so that, when the shaft rotates in a first direction, the shuttle translates along barrel 20 from the proximal position to the distal position. When the screw rotates in a second or opposite direction, the shuttle translates back to the proximal position. A button or rocker switch may create an interface allowing an operator to actuate the motor in either direction.

Figure 4:
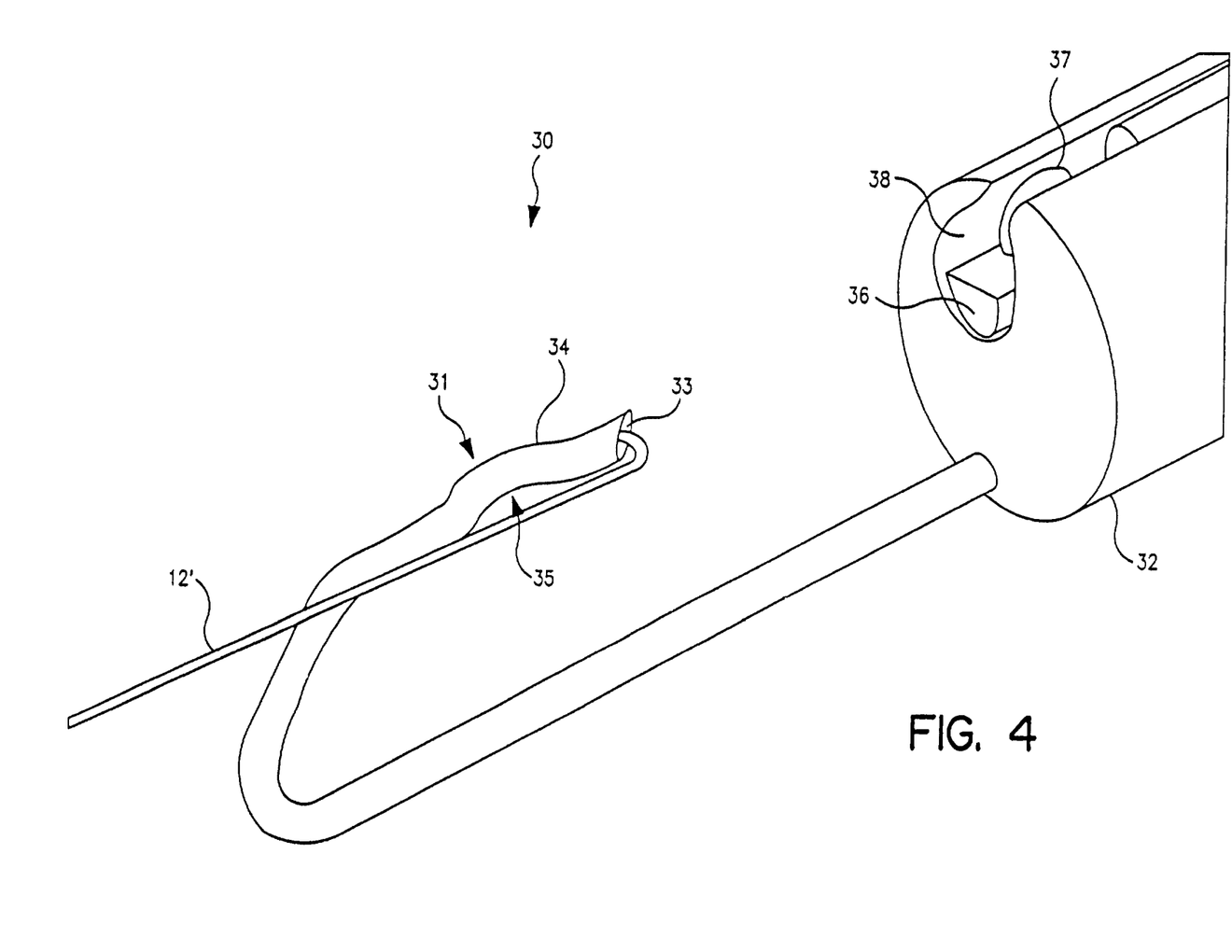
FIG. 4 depicts the tip of a suture placement apparatus including a crook-shaped needle comprising a suture passage for carrying a suture thread and a suture opening in the needle from which the suture thread exits the needle.

Referring to FIG. 4, a distal portion 30 of an embodiment of the suture placement apparatus of FIG. 3 is shown. A crook-shaped needle 31 extends from a barrel tip 32. Needle 41 comprises a suture thread passage (not shown) for carrying a suture thread 12' and a suture opening 33, from which suture thread 12' exits needle 31. Generally, suture thread 12' runs parallel to the axis of needle 31. However, needle 31 comprises at least one bend 34 which forms a suture thread capture zone 35. In capture zone 35, suture thread 12' continues to run parallel to needle 31, but is separated from the body of needle 31. Barrel tip 32 also comprises a shuttle passage 38, in which a shuttle 46 is slidably disposed. Shuttle 36 further comprises a hook or 37 hook wire, which extends outward from shuttle 36 in order to capture suture thread 12'.

Figure 5:
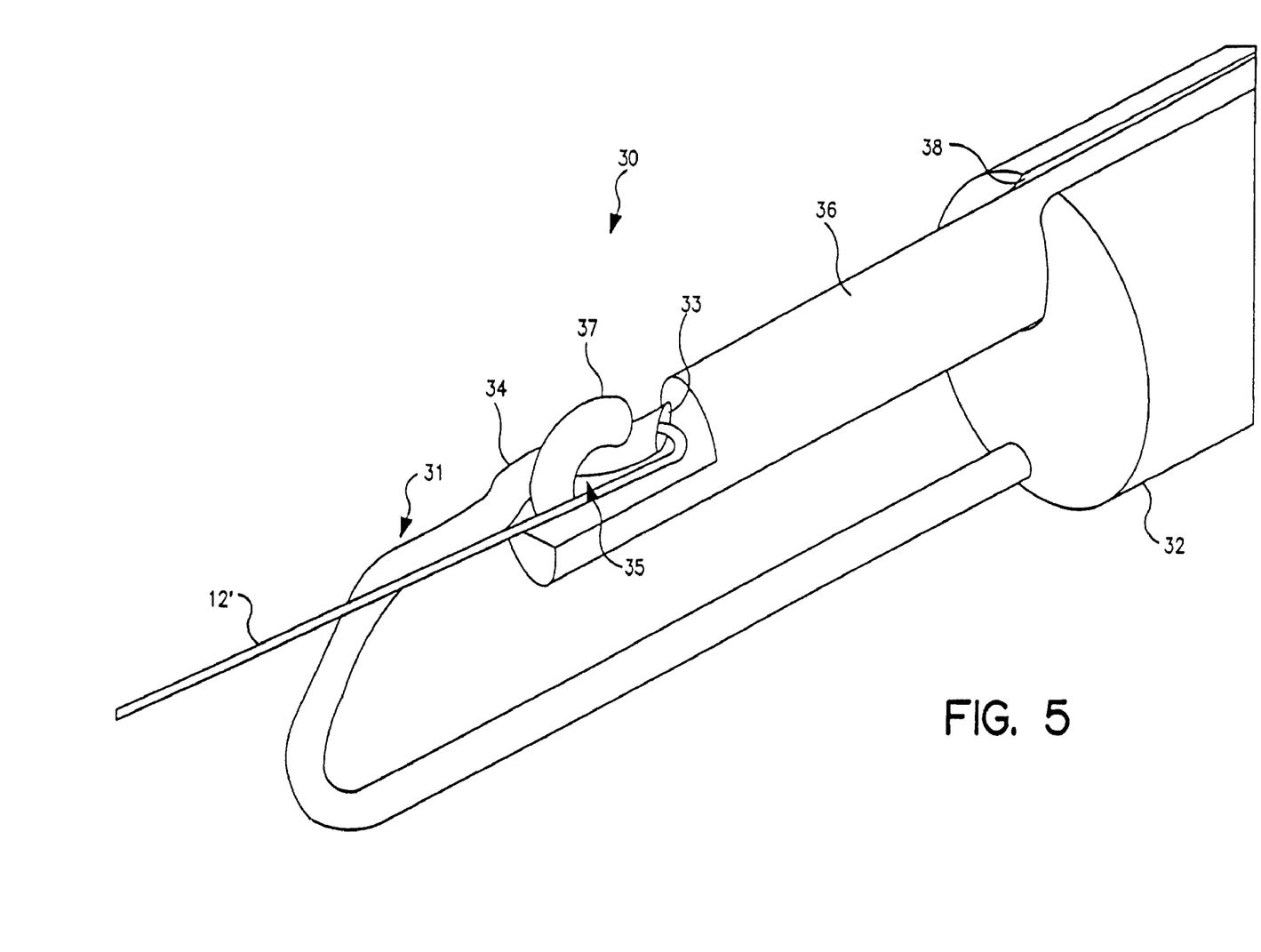
FIG. 5 depicts the tip of a suture placement apparatus, in which a shuttle including a hook wire for traversing the needle of FIG. 4 and engaging the suture thread in a capture area formed by the needle.

As noted above, the purpose of shuttle 36 is to capture suture thread 12' at the distal end and to bring the captured suture thread 12' to a proximal position, from which the operator may remove suture thread 12' from the apparatus. FIG. 5 depicts distal portion 30 of an embodiment of a suture placement apparatus, in which shuttle 36 including hook 37 for traversing needle 31 of FIG. 4 and for engaging suture thread 12' in capture area 35 formed by bend 34 in needle 31. Moreover, as discussed below with respect to FIG. 11, in another embodiment of the suture placement apparatus, the shuttle and the hook may move upward as the shuttle engages a small ramp at the distal end of the barrel, the hook may enter the capture zone from below, the shuttle and the hook then may translates proximally on a path parallel to the needle's axis to capture the suture thread.

Figure 6:
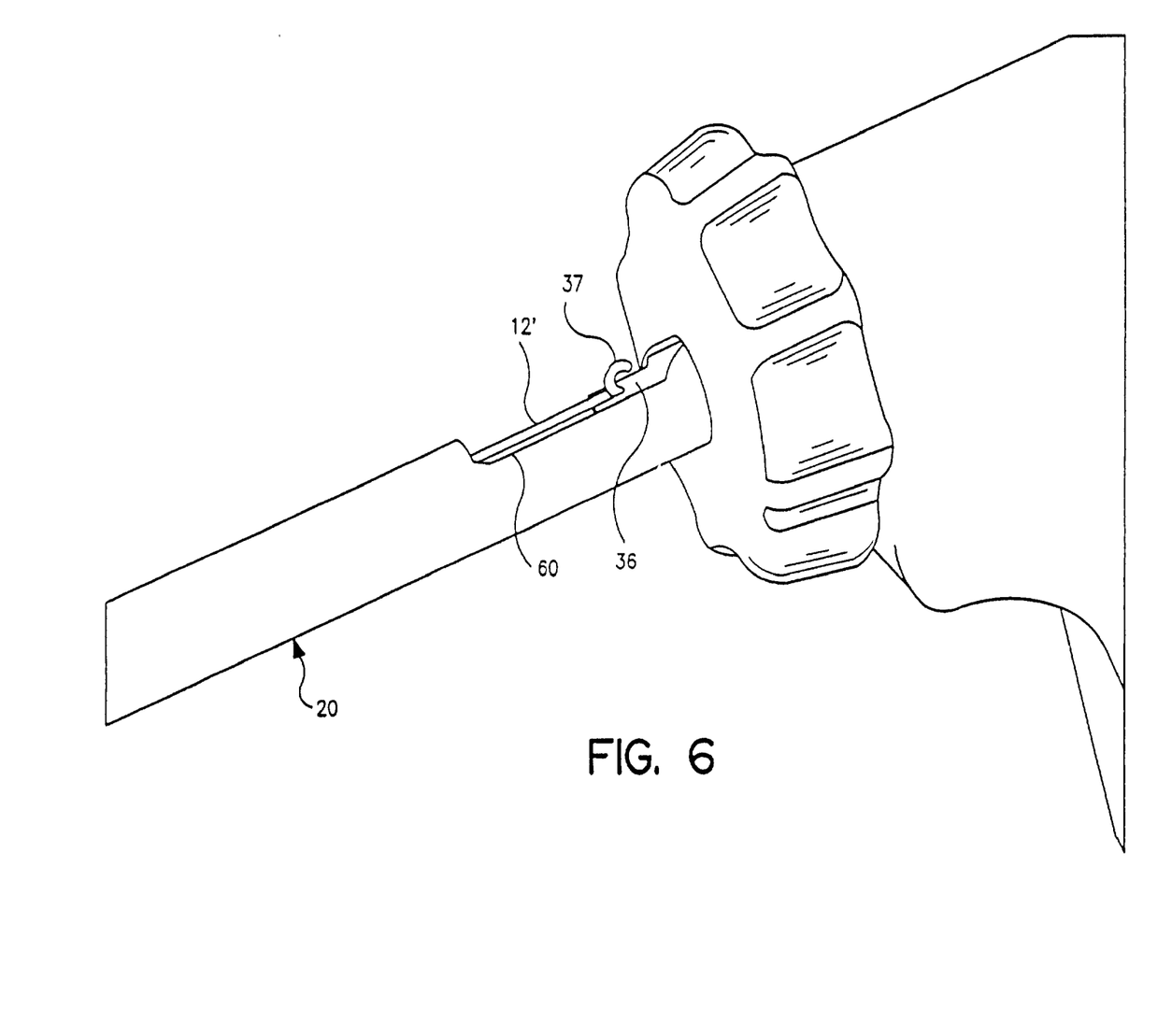
FIG. 6 depicts a suture pick-up position proximate to the grip portion of a suture placement apparatus, such as that depicted in FIG. 3.

Referring to FIG. 6, a suture pick-up position 60 of an embodiment of a suture placement apparatus, such as that depicted in FIG. 3, is shown. Suture pick-up position 60 is located at the proximal end of barrel 20. After having captured suture thread 12', shuttle 36 returns to barrel 20 and translates to the proximal position, at which the surgeon or other operator removes suture thread 12' from the apparatus.

As described above, the shuttle and hook must be driven on a path, by which the hook or the shuttle and the hook enter the capture zone and capture the suture thread. There exist various means to achieve the required path for the hook or the shuttle and the hook. In another embodiment, the suture placement apparatus may include a ridge formed on the hook that engages the needle as the hook traverses the needle and moves upward into the capture zone. After entering the capture zone, the shuttle may move proximally, and the hook may remain in its raised position until the hook moves beyond the needle. The length of the hook's ridge may be selected, such that once the hook has moved beyond the needle, the hook then lowers to its original axial position and continues to move proximally.

Another means for achieving the desired path is to constrain the shuttle within a track comprising two distinct branches at the distal tip of the apparatus. When moving distally, the shuttle rides in the lower branch of the track, which guides the shuttle upward into the capture zone. After the suture thread has been captured, the shuttle will leave the lower branch and enter the upper branch of the track. When moving proximally, the shuttle rides in the upper branch of the track. The two branches may converge again after the hook disengages from the needle proximal to tip of the apparatus.

In order to ensure that the shuttle rides in the correct branch, leaf springs positioned at the diverging points between the branches of the track. As a result, the track may be configured to create a "one way only" path.

Figure 7A:
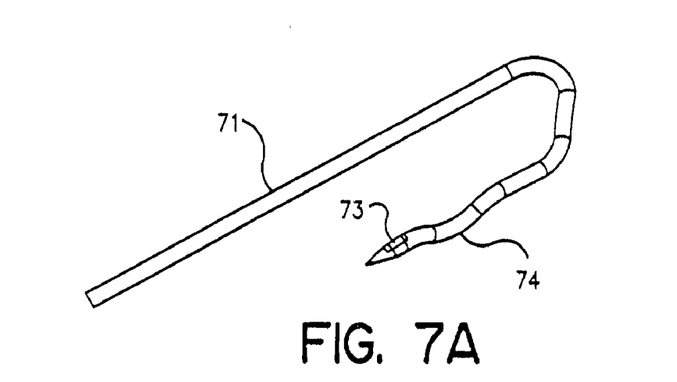
FIGS. 7A–7C depict another embodiment of the crook-shaped needle for use in a suture placement apparatus, such as that depicted in FIG. 3.
Figure 7B:
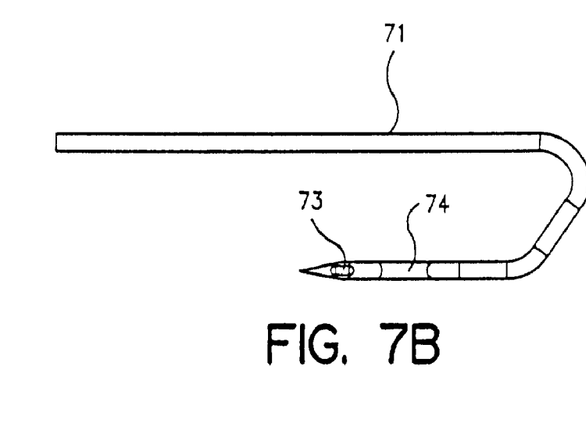
Figure 7C:
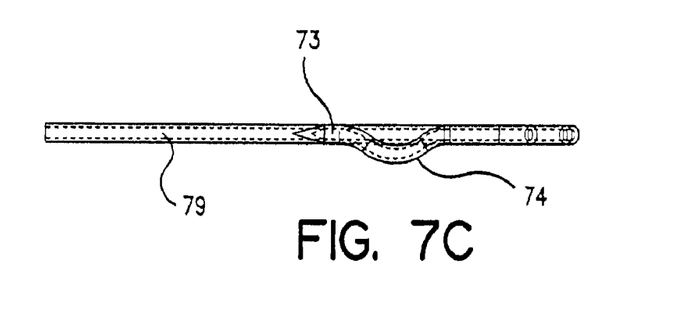
Figure 7D:
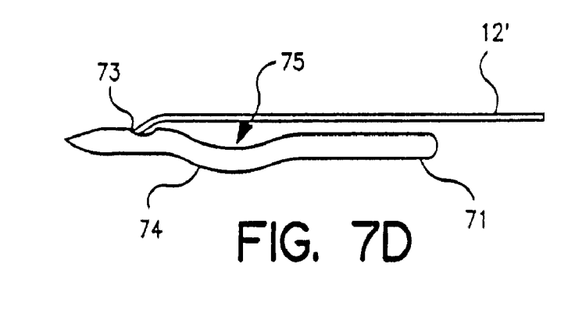
FIG. 7D depicts the upper portion of a crook-shaped needle and a suture thread exiting the needle tip and entering the capture zone.

FIGS. 7A–7C depict another embodiment of the crook-shaped needle for use in a suture placement apparatus, and FIG. 7D depicts the suture thread exiting the needle tip and entering the capture zone. Referring to FIGS. 7A and 7B, a crook-shaped needle 71 is depicted. Needle 71 has at least four distinctive characteristics. First, needle 71 is crook-shaped causing it to bend back substantially upon itself. As a result, the upper and lower portions of needle 71 lie in substantially the same plane. This alignment between the upper and lower portions of needle 71 is clearly shown in FIG. 7C. Second, as further shown in FIG. 7C, needle 71 includes a suture passage 79, through which the suture thread passes. Third, as is shown by each of FIGS. 7A–7D, needle 71 comprises a suture opening 73 located adjacent to the sharpened tip of needle 71. Fourth, needle 70 possesses a bend 74, which is formed in the upper portion of needle 71, adjacent to the needle's tip. Unlike the remainder of needle 71, bend 74 diverges from the plane of needle 71 and creates a capture zone 75, in which the hook described above may capture suture thread 12'. Referring to FIG. 7C, this divergence between the plane of needle 71 and bend 74 is clearly shown.

Figure 8:
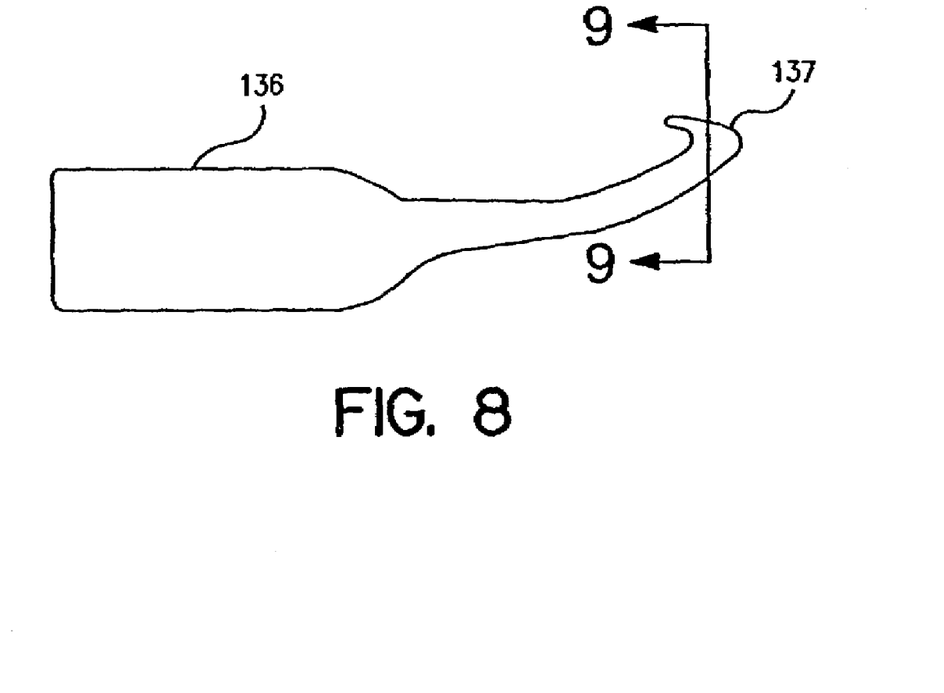
FIG. 8 depicts another embodiment of the shuttle comprising an integral suture hook.
Figure 9A:
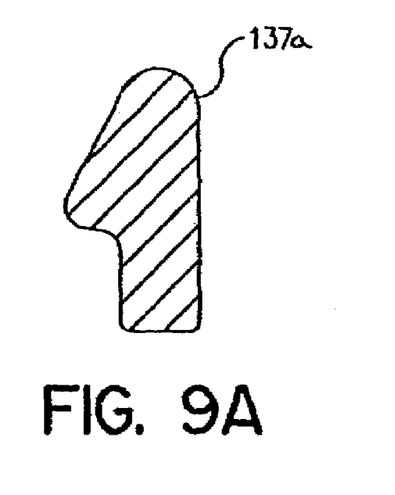
FIGS. 9A and 9B show alternative cross-sectional configurations along line 9—9 of the shuttle of FIG. 8.
Figure 9B:
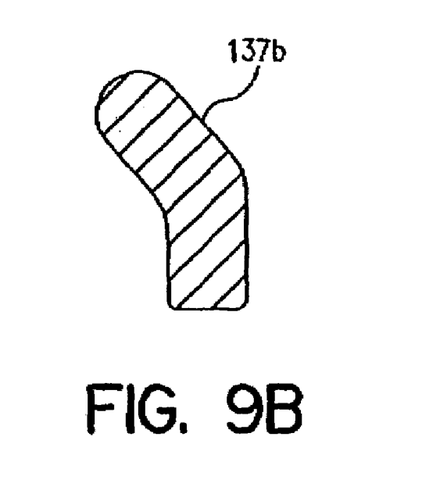

FIG. 8 depicts another embodiment of the shuttle for the suture placement apparatus. A shuttle 136 comprises an integral suture hook 137. Integral shuttle 136 and its hook 137 are urged upward together into the suture capture zone created by the bend in the needle. FIGS. 9A and 9B show alternative cross-sectional configurations along line 9—9 of shuttle 136 of FIG. 8. As depicted in FIG. 9A, integral hook 137a is formed with a lip that extends substantially perpendicular to the axis of shuttle 136. This lip enhances the ability of hook 137a to capture the suture thread. Similarly, as depicted in FIG. 9B, integral hook 137b is angled away from the axis of shuttle 136. This off-axis orientation also enhances the ability of hook 137b to capture the suture thread.

Figure 10:
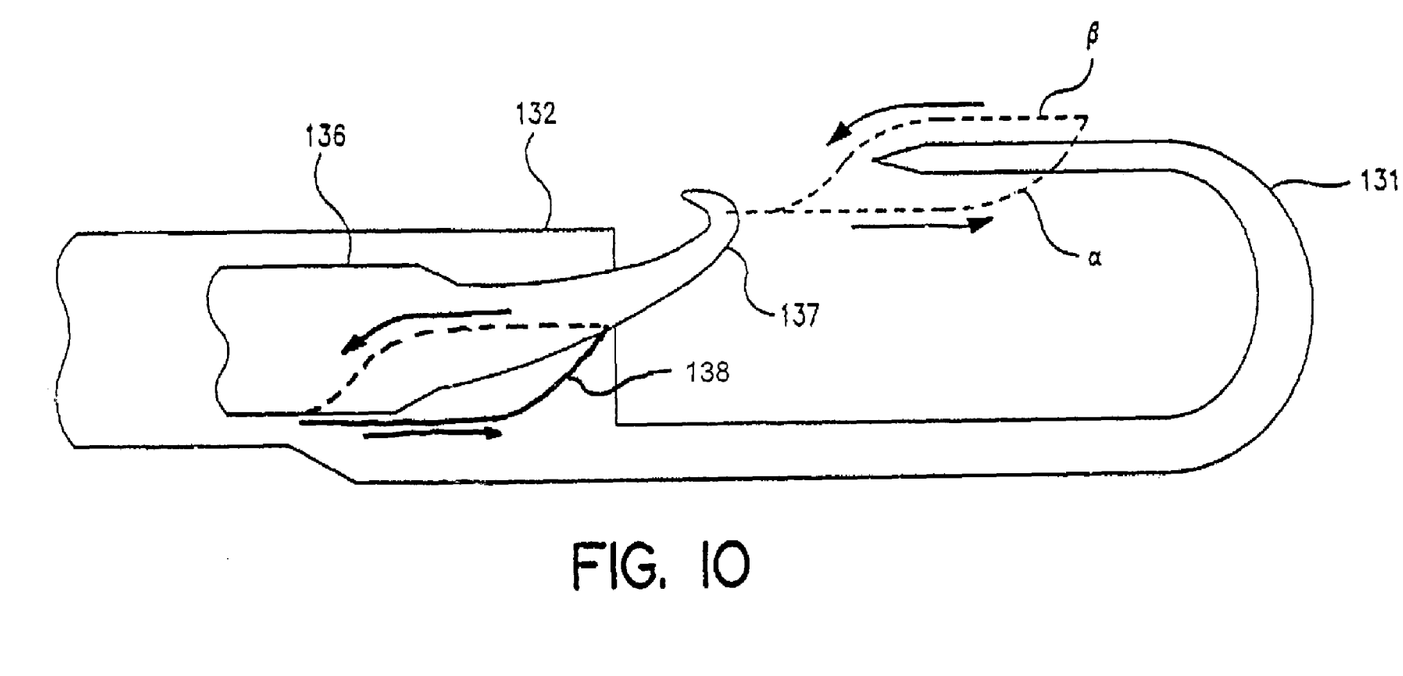
FIG. 10 is a schematic cross-sectional view of the path of the shuttle of FIG. 8, as it passes over the needle and captures the suture thread.

FIG. 10 is a schematic cross-sectional view of the path of shuttle 136 of FIG. 8, as it passes over a needle 131 and captures the suture thread. In an embodiment, shuttle 136 moves distally over a ramp 138 within a barrel tip 132, which urges hook 137 of shuttle 136 over needle 131. As shown in FIG. 10, shuttle 136 moves distally along the lower branch α of the broken-line shuttle path and then upward and over needle 131. Once hook 137 passes through the suture capture zone and reaches its farthest point distally over needle 131, shuttle 136 and hook 137 begin their return passage along the upper branch β of the broken-line shuttle path and return proximally and substantially parallel to the upper portion of needle 131. After clearing the tip of needle 131, hook 137 completes its passage over needle 131 by returning to its starting point in barrel tip 120. Thus, ramp 138 may comprise a track comprising a lower branch A and an upper branch B. When moving distally, shuttle 136 rides in lower branch A of the track, which guides shuttle 136 upward into the capture zone. After the suture thread has been captured, Shuttle 136 leaves lower branch A and enters upper branch B of the track.

Figure 11:
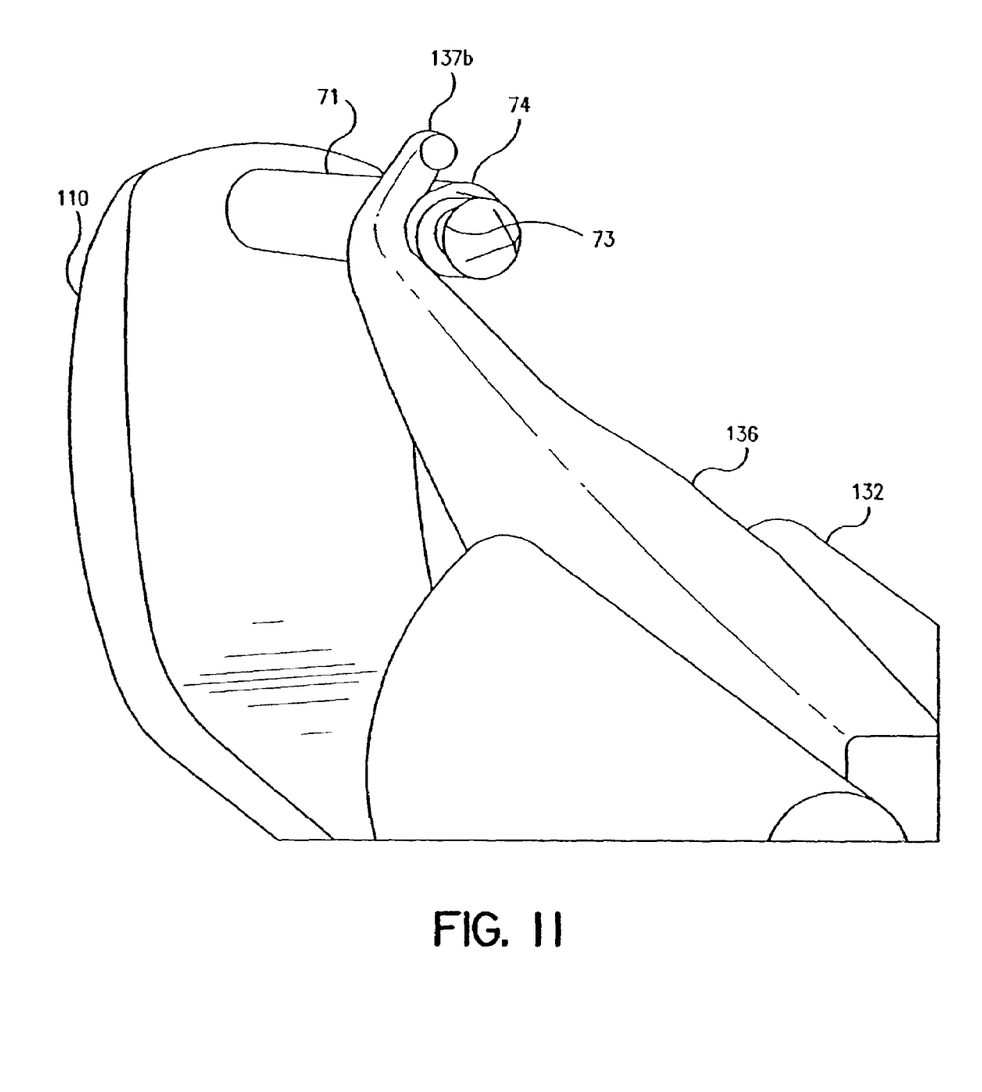
FIG. 11 is a perspective view of shuttle of FIG. 8 passing over the needle of FIGS. 7A–7D.

Referring to FIG. 11, a perspective view of shuttle 136 and hook 137b of FIGS. 8 and 9B passing over needle 71 is shown. Needle 71 is partially obscured by hook 137b and a needle housing 110, but is substantially similar in configuration to needles 71 depicted in FIGS. 7A–7D. Hook 137b has an angled orientation, the inclination of which is formed to be received within a bend 74 of needle 71 and to otherwise ride against needle 71.

Figures 12A, 12B:
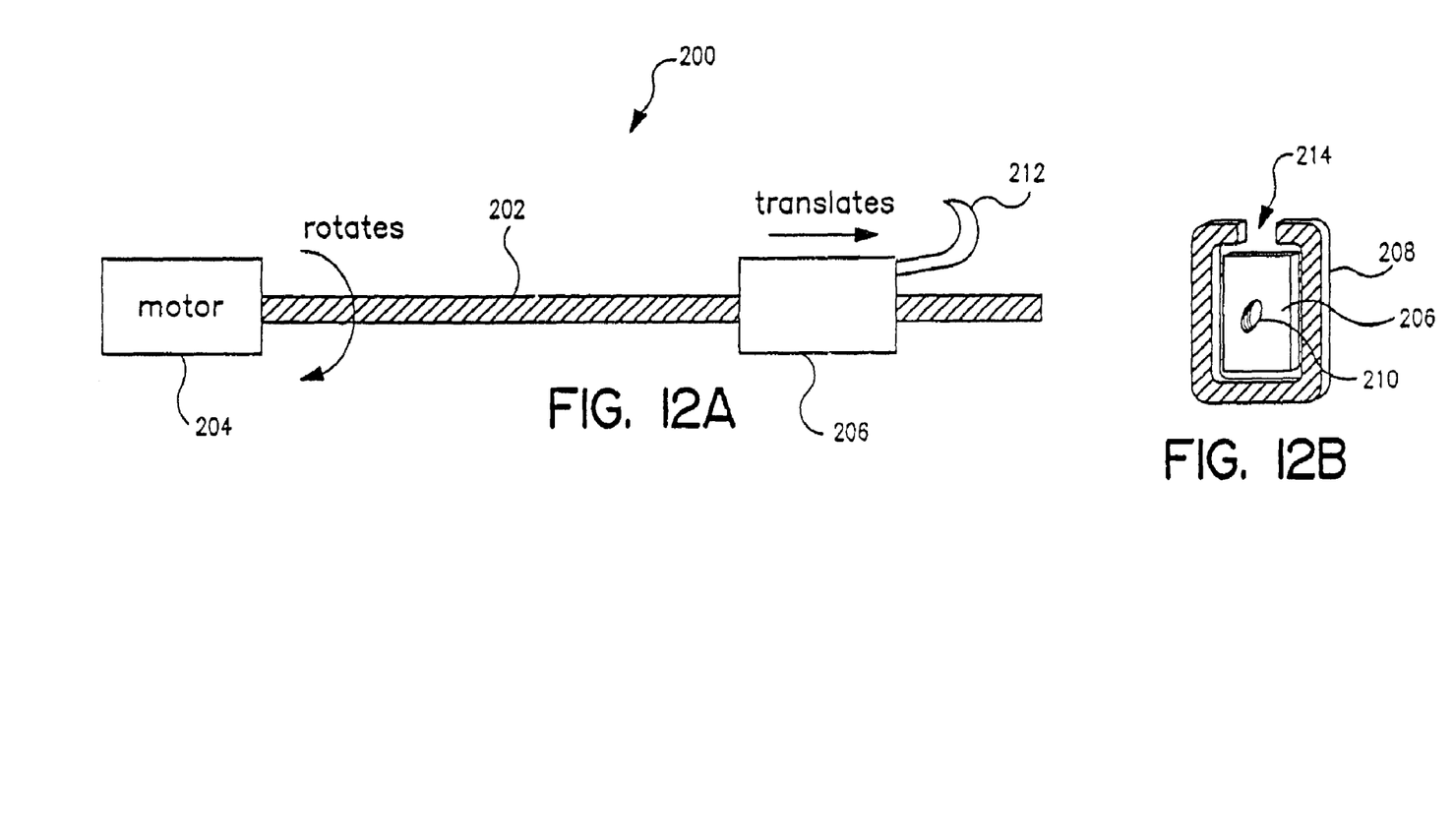
FIGS. 12A and 12B depicts a schematic of still another embodiment of the suture placement apparatus, wherein the shuttle translates along a rotating screw.

FIGS. 12A and 12B depicts a schematic of still another embodiment of a suture placement apparatus 200, wherein a shuttle 206 translates along a rotating drive shaft 202 driven by motor 204. Motor 204 may be a compact, reversible, electric motor. The electric motor may be battery powered or powered by an external power source. Motor 204 is used to drive shuttle 206 back and forth between the proximal and distal portions of the apparatus's barrel. Motor 204 is coupled to drive shaft 202, which extends the length of the apparatus's barrel (not shown). As described with respect to FIG. 12B, shuttle 206 is contained within a shuttle housing 208. Shuttle housing 208 prevents shuttle 206 from rotating within shuttle housing 208 on drive shaft 202. Referring again to FIG. 12B, shuttle 206 includes a threaded, drive shaft orifice 210, which receives drive shaft 202. Shuttle housing 208 further includes a hook opening 214, so that as hook 212 engages and rides over a needle, hook 212 may rise up through hook opening 214.

EXAMPLES

Figure 13:
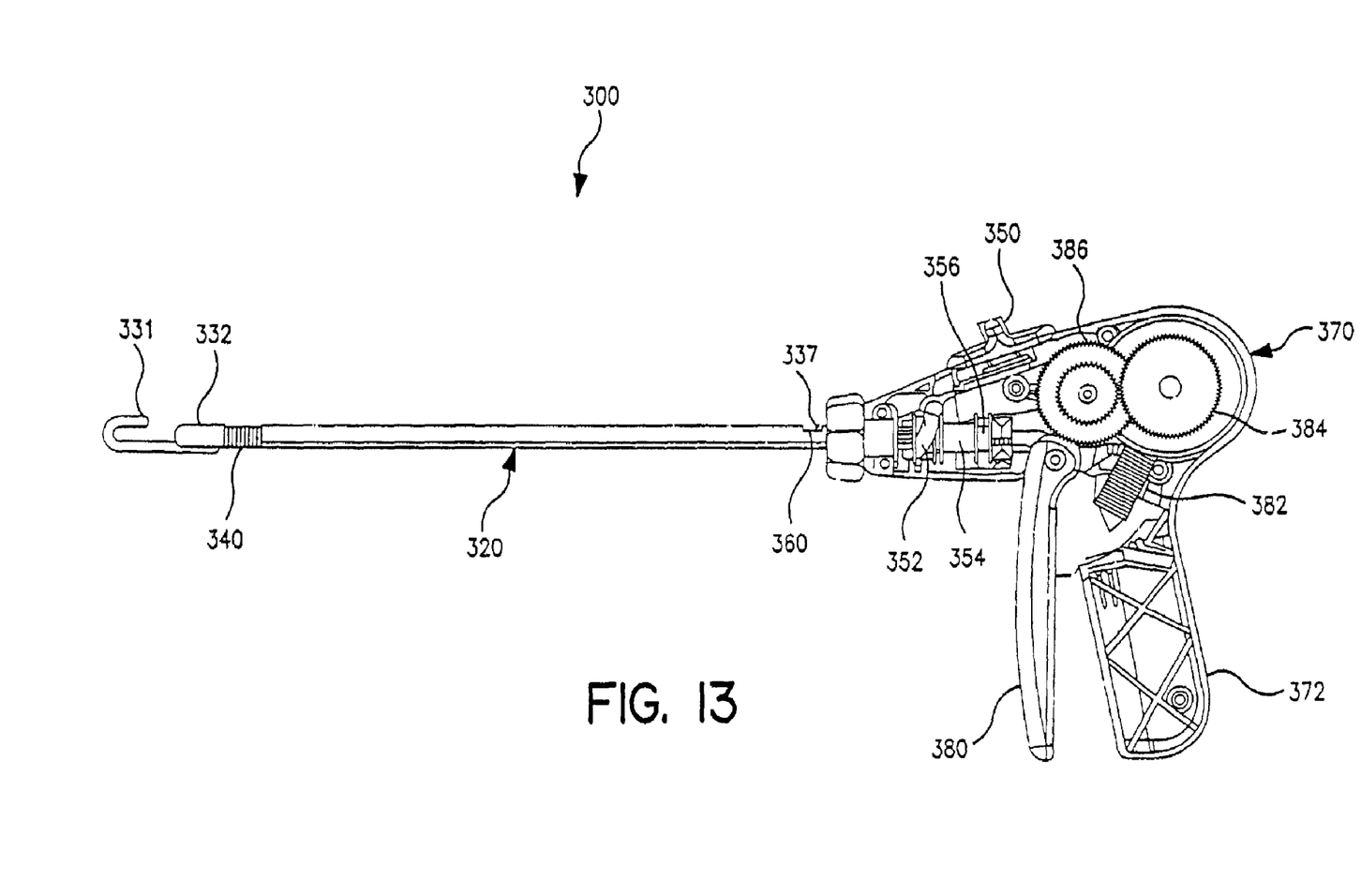
FIG. 13 depicts a cross-sectional view a suture placement apparatus, such as that depicted in FIG. 3.

The invention will be further clarified by consideration of the following examples, which are intended to be purely exemplary of the use of the invention. FIG. 13 depicts a cross-sectional view a suture placement apparatus, such as that depicted in FIG. 3. This embodiment of a suture placement apparatus 300 uses a combination of gears actuated by a drive lever 380 to drive a shuttle from a proximal position to a distal suture capture position.

Apparatus 300 comprises a barrel 320 and a crook-shaped needle 331 at the distal end of barrel 320. A suture thread (not shown), which is coiled around a spool 354 at the proximal end of barrel 320, feeds out through needle 331 at or near the tip of needle 331. A distal portion 330 is joined to the remainder of barrel 320 by a barrel tip 332 and a flexible coupling 340, that allows an operator to articulate the barrel's distal end and, in particular, barrel tip 332 and needle 331. In this embodiment, a steering slide 350 positioned on and interoperative with the components within an apparatus body 370 may be moved back and forth, parallel to the axis of barrel 320, in order to articulate the barrel's distal end, e.g., barrel tip 332 and needle 331.

In particular, apparatus 300 comprises a steering wire spool 356, which carries steering wire (not shown) that runs down either side of barrel 320 and is fixedly joined to barrel tip 332. When steering slide 350 is moved forward or backward, it engages a steering grip rocker 352. As steering grip rocker 352 pivots, it causes steering wire spool 356 to feed steering wire to one side of barrel 320 and to coil steering wire from the opposite side of barrel 320. This causes barrel tip 332 and needle 331 to articulate toward the side of the coiling steering wire.

Figure 14:
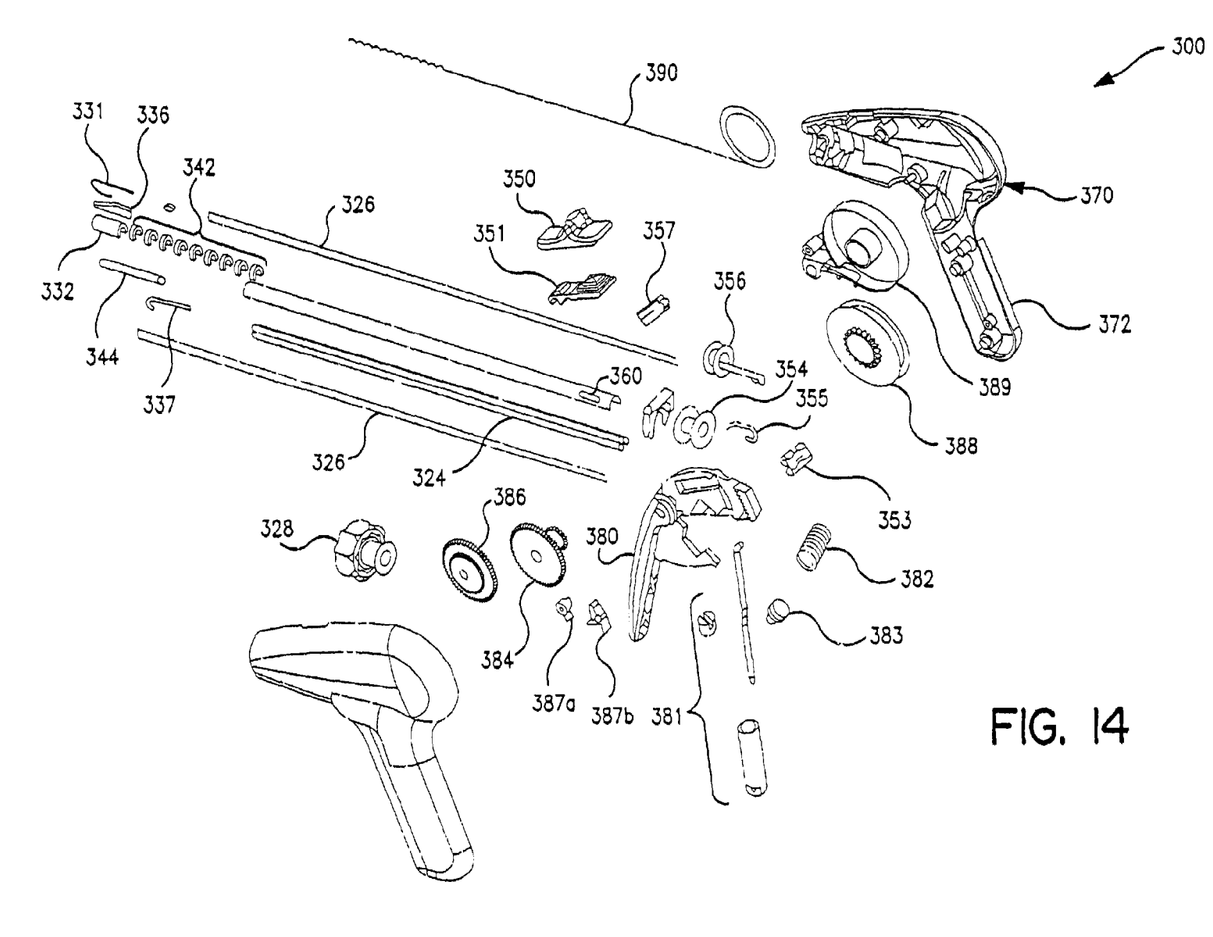
FIG. 14 depicts an exploded view of the embodiment of FIG. 13.

In addition, a shuttle mechanism, described below with respect to FIG. 14, is adapted to translate through barrel 320 from a proximal end of barrel 320 to the distal end of barrel 320. The shuttle mechanism comprises a hook or hook wire 337, which captures a suture thread (not shown) after it exits needle 331. Apparatus 300 also includes a grip 372 and drive lever 380, by which the operator causes the shuttle to translate through barrel 320. After hook 337 has captured the suture thread from needle 331, drive lever 380 is used to translate the shuttle to a suture pick-up position 360 at the proximal end of barrel 320, so that the suture thread then is removed from hook 337.

As discussed in detail below, drive lever 380 engages and drives a plurality of gears in a first direction. This plurality of gears drives the shuttle to traverse over needle 331 toward a suture capture zone formed by needle 331. When squeezed, drive lever 380 compresses a spring 382. The stored energy in spring 382 later is used to drive the plurality of gears in a second direction opposite to the first direction. The movement of these gears in the second direction drives the shuttle to traverse over needle 331, to engage the suture thread, and to draw the suture thread toward the proximal end of barrel 320.

In particular, when drive lever 380 is squeezed, spring 382 compresses and a set of gear teeth on drive lever 380 engage a first drive gear 384. First drive gear 384 subsequently engages a second drive gear 386, which in turn rotates a drive cable spool 388. The rotation of drive cable spool 388 causes a threaded drive cable (not shown) to cause the shuttle (not shown) to translate distally in barrel 320. When drive lever 380 is released, spring 382 causes first drive gear 384 and second drive gear 386 to engage and move in the opposite direction. This causes drive cable spool 388 to rotate in the opposite direction, and the threaded drive cable draws the shuttle proximally through barrel 320 to suture pick-up position 360.

FIG. 14 depicts an exploded view of the embodiment of suture placement apparatus 300 of FIG. 13. Barrel 320 comprises a barrel cover 322 including a suture pick-up point 360 and a flexible tube assembly 324. A pair of steering wires 326 within barrel 320 on opposite sides of flexible tube assembly 324. Flexible tube assembly 324 also carries a shuttle 336 and hook 337 as they translate the length of barrel 320. Flexible tube assembly 324 also provides a conduit for threaded drive cable 390 and for suture thread (not shown) uncoiled from suture spool 354 through a suture guide tube 355. The distal portion of barrel 320 is joined to the remainder of barrel 320 by barrel tip 332 and flexible coupling 340. Flexible coupling 340 comprises nine separate links 342 surrounding a flexible tube 344, which permit the articulation of the barrel tip 332 and needle 331.

As noted above, apparatus 300 comprises steering wire spool 356, upon which steering wires 326 are partially coiled. When steering slide 350 is moved forward or backward, steering slide 350 operates a steering rocker lever 351, which in turn engages steering grip rocker 352 and a steering rocker 353. As steering grip rocker 352 and steering rocker 353 pivot, they cause steering wire spool 356 to feed steering wire to one side of barrel 320 and to coil steering wire from the opposite side of barrel 320. This causes barrel tip 340 and needle 331 to articulate toward the side of the coiling steering wire.

Drive lever 380 is mounted on drive lever shaft assembly 381. Spring 382 is mounted on a spring base 383 and is compressed by drive lever 380 when drive lever 380 is squeezed. A set of gear teeth on drive lever 380 engage the smaller gear on first drive gear 384. The larger gear on first drive gear 384 subsequently engages the smaller gear on second drive gear 386. The larger gear on second drive gear 386 then rotates drive cable spool 388. This series of gears allows the relatively short stroke of drive lever 380 to generate significant rotation in drive cable spool 388. Drive cable spool 388 is contained within a drive cable spool housing 389, which is equipped with a guide for directing a threaded drive cable 390 from drive cable spool 388 through a barrel nut 328 and into barrel 320. Apparatus 300 is equipped with a drive latch 357 allows drive cable spool 388 to be locked into a single position, such as when articulating needle 331.

Drive lever 380 is equipped with ratchet latches 387a and 387b, which hold drive lever 380 in place and prevents spring 382 from releasing it energy. Nevertheless, the same gear ratios, which permitted the short stroke of drive lever 380 to generate sufficient rotation in drive cable spool 388, permit the energy released from spring 382 to translate shuttle 336 and hook 337 from the distal end of barrel 320 to suture pick-up point 360.

Although several embodiments of the present invention have been described in detail herein, the scope of the invention is not limited thereto. Other embodiments of the invention will be apparent to the skilled in the art from a consideration of the specification or practice of the invention disclosed herein. Moreover, it will be appreciated by those skilled in the art that various modifications may be made without departing from the scope of the invention. It is intended that the specification and the examples be considered as exemplary only, with the true scope and spirit of the invention being indicated by the following claims.

What is claimed is:

1. A suture placement device comprising:
   a crook-shaped needle comprising a suture passage through which a suture thread passes; a suture opening in a tip portion of said needle, from which said suture thread exits said needle; and a bend in said needle including an open portion of said suture passage, said bend defining a suture capture zone in which said suture thread is separated from said needle in said suture capture zone;
   a shuttle comprising a shuttle body and a shuttle hook, said shuttle hook formed at a distal end of said body;
   a barrel from which said needle extends and said shuttle may be extended, which comprises a source of said suture thread and means for traversing said shuttle over said needle; and
   means for guiding said shuttle along said tip portion of said needle into said suture capture zone, such that said shuttle traverses said needle and said shuttle hook engages said suture thread in said suture capture zone and draws said suture thread to said barrel, wherein said means for guiding said shuttle comprises a ramp formed within said barrel and comprising a track comprising at least two branches on which said shuffle rides, such that as said shuttle distally traverses over said needle, said ramp guides said shuttle hook through said suture capture zone and as said shuttle proximally traverses over said needle, said shuttle hook engages said thread of suture and draws said suture thread toward said barrel.

2. The suture placement device of claim 1, wherein said means for traversing said shuttle over said needle comprises a lever engaging and driving a plurality of gears in a first direction, which drive said shuttle to traverse over said needle toward said suture capture zone and compress a biasing means that engages and drives said plurality of gears in a second direction opposite to said first direction, which drive said shuttle to traverse over said needle to engage said suture thread and draw said suture thread toward said barrel.

3. The suture placement device of claim 2, wherein said biasing means is a spring.

4. The suture placement device of claim 1, wherein said means for traversing said shuffle over said needle comprises a reversible motor, a screw drive shaft, a threaded passage formed through said shuttle to engage said screw drive shaft, and a guide housing which prevents said shuttle from rotating.

5. The suture placement device of claim 1, wherein said needle further comprises a lower portion, which is substantially parallel to said tip portion, and a distal portion, which joins said lower portion to said tip portion; and a rib is formed on an outer edge of and reinforces said lower portion and said distal portion.

6. The suture placement device of claim 1, wherein said needle is formed in a plane and said barrel is articulated, so that said needle is rotatable in said plane of said needle.

7. The suture placement device of claim 5, wherein said means for traversing said shuttle over said needle comprises a lever engaging and driving a plurality of gears in a first direction, which drive said shuttle to traverse over said needle toward said suture capture zone and compress a biasing means that engages and drives said plurality of gears in a second direction opposite to said first direction, which drive said shuttle to traverse over said needle to engage said suture thread and draw said suture thread toward said barrel.

8. The suture placement device of claim 7, wherein said biasing means is a spring.

* * * * *